United States Patent [19]

Miyoshi

[11] Patent Number: 4,606,914

[45] Date of Patent: Aug. 19, 1986

[54] COSMETIC COMPOSITION

[75] Inventor: Ryota Miyoshi, Iwatsuki, Japan

[73] Assignee: Miyoshi Kasei Co., Ltd., Saitama, Japan

[21] Appl. No.: 428,811

[22] Filed: Sep. 30, 1982

[30] Foreign Application Priority Data

Oct. 26, 1981 [JP] Japan ................................ 56-171110

[51] Int. Cl.⁴ ............................................. A61K 7/021
[52] U.S. Cl. ...................................... 424/63; 424/64; 424/69; 514/789; 514/943
[58] Field of Search ..................... 424/63, 64, 365, 69, 424/320, 287, 289; 106/308 F, 308 N; 514/943, 748

[56] References Cited

U.S. PATENT DOCUMENTS 4,089,954  5/1978  Morelle et al. ................. 424/320 X

FOREIGN PATENT DOCUMENTS

| 47-14342 | 8/1972 | Japan | 424/64 |
|---|---|---|---|
| 51-44650 | 4/1976 | Japan | 424/365 |
| 53-64208 | 6/1978 | Japan . | |
| 53-113787 | 10/1978 | Japan | 424/365 |
| 50-79315 | 6/1980 | Japan | 424/69 |
| 57-24343 | 2/1982 | Japan | 424/365 |
| 58-27636 | 2/1983 | Japan | 514/943 |
| 1436614 | 5/1976 | United Kingdom | 424/365 |

OTHER PUBLICATIONS

Chem. Abs. 89:148497a (1978).

Primary Examiner—Esther M. Kepplinger
Assistant Examiner—Shawn P. Foley
Attorney, Agent, or Firm—Armstrong, Nikaido, Marmelstein & Kubovcik

[57] ABSTRACT

A cosmetic composition for make-up containing an N-acylamino acid salt or Al, Mg, Ca, Zn, Zi or Ti which may contain a pigment and/or an extender pigment treated with one or more of the N-acylamino acid metal salts.

7 Claims, No Drawings

COSMETIC COMPOSITION

BACKGROUND OF THE INVENTION

(1) Field of the Invention

The present invention relates to a cosmetic composition for make-up. More specifically, the invention relates to a cosmetic composition containing an N-acylamino acid or an Al, Mg, Ca, Zn, Zr or Ti salt thereof (hereinafter referred to as "N-acylamino acid metal salt") or to a cosmetic composition containing a pigment and/or an extender pigment treated with one or more of the N-acylamino acid metal salts.

(2) Prior Art

Water-soluble N-acylamino acid salts such as Na-, K-, Li- and triethanolamine-salts (hereinafter referred to as "N-acylamino acid water soluble salt") have been industrially produced and marketed as anionic surface active agents. They have been widely employed as detergents and emulsifiers and as cosmetic bases in shampoos, soaps, creams and the like.

Conventionally, it has been reported that amino acids and their derivatives exhibit many desirable properties and effects when employed in cosmetics. Among others, when they are employed as a raw material in cosmetic compositions, they are very advantageous in that they do not irritate the skin and protect the skin from pollution. Further, their protective action against germs and the effect for preventing drying of the skin are worth noting. However, these salts, among N-acylamino acid salts, are water-soluble salts. Al, Mg, Ca, Zn, Zr or Ti salts of N-acylamino acids, which are insoluble in water, unlike the Na, K, Li and triethanolamine-salts, have thus far not found cosmetic applications.

SUMMARY OF THE INVENTION

An object of the present invention is to provide cosmetic compositions useful as make-up.

More specifically, an object of the present invention is to provide a cosmetic composition which is physiologically safe.

Another object of the present invention is to provide a cosmetic composition, or make-up, which gives an excellent feeling to the skin.

Still another object of the present invention is to provide a cosmetic composition which has a small degree of degradation when applied as make-up.

A still further object of the present invention is to provide a cosmetic composition which is stable over a period of time.

A further object of the present invention is to provide a cosmetic composition which has a protective action for the skin.

According to the present invention a cosmetic composition is provided which contains an Al, Mg, Ca, Zn, Zr, or Ti salt thereof of the following formulae (I), (II), or (III), or which contains a pigment or an extender pigment treated with the N-acylamino acid metal salt.

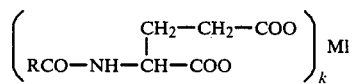 (I)

-continued

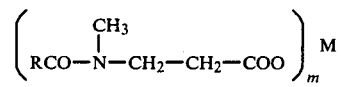 (II)

or

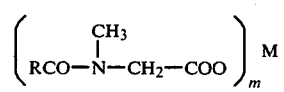 (III)

wherein RCO denotes a residue of capric acid, lauric acid, myristic acid, palmitic acid, stearic acid or oleic acid; M denotes a hydrogen atom, Al, Mg, Ca, Zn, Zr, or Ti; k is an integer of 1 to 3; l is an integer of 1 to 2; and m is an integer of 1 to 4. The pigment or extender pigment contained in the cosmetic composition according to the present invention may be coated with oil.

These and other objects and features of the present invention will be apparent from a reading of the following description of the invention, it being understood that variations and modifications may be made therein as fall within the scope of the appended claims without departing from the spirit of the invention.

DETAILED DESCRIPTION OF THE INVENTION

The present inventor discovered, during a study of novel hydrophobic pigments, that N-acylamino acid metal salts, inter alia, the Al, Mg, Ca, Zn, Zr, and Ti salts exhibit remarkable effects when employed as a raw material in cosmetic compositions for make-up and accomplished the present invention.

As conventional raw materials of cosmetic compositions corresponding to the N-acylamino acid metal salts, metallic soaps and lauric acid, myristic acid and stearic acid among higher fatty acids, and their Zn, Al, Ca and Mg salts have been employed. Such materials are mixed into shampoos, creams, lip sticks, white powders, foundations, rouges for cheeks, eye-shadows, or the like as retainers or emulsifiers of pearl essence, dispersants, molding agents, water-repellents, adherability-improving agents and perfumes. Further, it is reported that they are applicable as treating agents of so-called extender pigments employed in such cosmetic compositions.

Comparing these metallic soaps, the higher fatty acids and their salts and the N-acylamino acid metal salts of the present invention from the standpoint of the above uses, the N-acylamino acid metal salts have remarkable cosmetic effects. For instance, a comparison between the N-acylamino acid metal salts useful in the present invention and the metallic soap which is employed in a conventional solid type white powder reveals that the former has the advantages that it enhances the dispersion property, or dispersability, of other pigments and the like due to a stronger affinity to the other pigments and oils, and enables homogeneous compositions to be obtained easily without a great degree of stirring and/or crushing.

Therefore, a uniform finish with no flashy appearance which is free from "uneven make-up" and "seam" can be obtained. Furthermore, the N-acylamino acid metal salts employed in the present invention have a nice touch without an unnatural feeling and with smaller strange touch after make-up, without loss of a nice touch peculiar to the amino acid conventionally used.

One aspect of the present invention is to provide a cosmetic composition to be applied as make-up in which the surfaces of pigment included in the composition are coated with the N-acylamino acid metal salts thereby remarkably enhancing the dispersability of the pigment. Another aspect of the present invention is to provide a cosmetic composition which is in a completely water-repellent powder form obtained by surface-coating a hydrophilic inorganic pigment such as titanium oxide or sericite.

As such a dispersing and water-repellent agent, silicon oil has been most frequently employed. Additionally, pigments treated by baking with methylhydrodienepolysiloxane are frequently employed particularly as a raw material for powder foundations. A comparison between pigments treated with this methylhydrodienepolysiloxane and those treated with, for instance, the aluminum N-acyl-L-glutamate of the present invention, shows that the latter are excellent as compared to the former in terms of moisty touch, adherability to the skin, make-up maintenance and the like which are important in the cosmetic.

The N-acylamino acid salts which are useful as the additive and/or pigment-treating agents for the make-up cosmetics are the salts of N-acyl-N-methylglycine, N-acyl-N-methyl-β-alanine and N-acyl-L-glutamine acid and, specifically, the Al, Mg, Ca, Zn, Zr and Ti salts. The metal salts of N-acyl-glutamine acid are the most useful. Acyl group may include a residue of capric acid, lauric acid, myristic acid, palmitic acid, stearic acid or oleic acid.

The salts of other metals such as Ba, Pb, Cd, Fe, Cu, Ni, Cr, Sn and the like are, although useful as pigment-treating agents, undesirable, in view of toxicity, color and the like, in the cosmetic field. They are employed as hydrophilic agents and dispersants in industrial pigment-treatment.

The N-acylamino acid metal salts useful in the invention may be manufactured in the following manner.

An N-acylamino acid water-soluble salts is dissolved in water to form about a 1 to about a 10% by weight aqueous solution. Into this solution is added about 1 to about 30%, preferably about 5 to about 10%, by weight aqueous solution of a water-soluble salt of Al, Mg, Ca, Zn, Zr and/or Ti. Suitable water-soluble salts include aluminum nitrate, aluminum chloride, aluminum sulfate, potassium aluminum sulfate, magnesium chloride, magnesium sulfate, magnesium nitrate, potassium magnesium sulfate, calcium chloride, calcium nitrate, calcium acetate, zinc chloride, zinc nitrate, zinc sulfate, zinc acetate, zirconium sulfate, zirconium chloride, titanium oxysulfate, titanium tetrachloride and the like. These salts are employed in amounts such that the amount of the water-soluble salt of the metal is about 1 to 1.2 molar equivalents relative to the N-acylamino acid salt. The addition is done dropwise under stirring. Stirring is continued and then the resultant slurry is dehydrated by a centrifuge. Thereafter, spray drying is carried out at 100° to 150° C. to obtain the N-acylamino acid metal salt.

The typical method for treating a pigment with the N-acylamino acid metal salt may be done in the following way.

First, into water is suspended a pigment (an inorganic pigment such as titanium oxide, zinc oxide, zirconium oxide, red iron oxide, yellow iron oxide, black iron oxide, ultramarine blue, Berlin blue, chromium oxide, chromium hydroxide; micas such as talc, kaoline, white mica powder, sericite, or the like; an extender pigment such as magnesium carbonate, calcium carbonate, aluminum silicate, magnesium silicate, calcium silicate, clay or the like; mica titanium, bismuth oxychloride, nylon powder, polyethylene powder, coal tar coloring material or natural coloring matter) to form from about a 5 to 30% by weight suspension. To this suspension is added an N-acylamino acid water-soluble salt in an amount of 0.5 to 10%, preferably 1 to 4%, by weight with respect to the pigment and stirring is carried out to form a homogeneous suspension. By so treating, the pre-treatment of the pigment, i.e., the primary particulation of the pigment is promoted. While this suspension is being stirred, about 1 to 30%, preferably about 5 to about 10%, by weight of a water-soluble salt of Al, Mg, Ca, Zn, Zr and/or Ti as mentioned above is gradually added dropwise in such an amount that the water-soluble metal salt is about 0.65 to about 2 molar equivalents, preferably about 1 to about 1.2 molar equivalents, with respect to the N-acylamino acid water-soluble salt. Thereby, the N-acylamino acid water-soluble salt reacts with the water-soluble metal salt of Al, Mg, Ca, Zn, Zr and/or Ti to cause the N-acylamino acid metal salt to be successively orientated and adsorbed onto the surfaces of the pigment. After the addition of the water soluble salt of Al, Mg, Ca, Zn, Zr and/or Ti, stirring is continued for about 10 min., followed by aging. Then, concentration is carried out by means of a centrifuge and drying is carried out at 80° to 120° C., thereby producing the treated pigment having a strong water repellent property, and a nice greasy feeling.

According to another aspect of the present invention, the surfaces of pigment treated as mentioned above are further coated with an appropriate oil to obtain a powdery preparation. More specifically, to the suspension after treating and aging is added an oil, or lubricant, which is used in cosmetics but has low hydrophilicity, for instance, paraffin, squalene, vaseline (Trademark), microwax, polyisobutylene, myristic acid, stearic acid, lauric acid, selemine, isopropyl myristate, myristyldodecanol, coconut oil, castor oil, lanoline, beeswax, olive oil, stearyl alcohol, mink oil, oleyl alcohol, monostearic glyceride, and the like, alone or as a mixture of two or more of these in an amount of 0.5 to 10%, preferably 1 to 5%, by weight based on the weight of the untreated pigment as it is or as a solution in alcohol, a petroleum based solvent or another appropriate organic solvent. Then, stirring is fully carried out.

Since the treated pigment suspended in the suspension is oleophilic, the oil added is adsorbed onto the surfaces of the treated pigment to fully make the surfaces of the pigment oleophilic. The oil-ooated pigment as fully concentrated by centrifuge becomes a pigment for a cosmetic composition and exhibits the effects of the N-acylamino acid metal salt as well as synergistic effects due to the added oil, i.e., it is an excellent pigment for a cosmetic composition with a moisty water-repellent property.

Further, the pigment treated according to the present invention exhibits greater advantages in practical application without drying the oil-coated pigment. More specifically, after the N-acylamino acid metal salt is oriented and adsorbed on the pigment in water, the treated pigment without being dried is mixed with a water-base or kneaded type make-up cosmetic such as a water-base white powder, kneaded type white powder, foundation or the like to produce a final product. Such a product has the N-acylamino acid metal salt orientated and adsorbed on its surfaces and contains a large amount of adsorbed water. Therefore, it is unnecessary to use a large amount of energy in preparing a centrifuge-dehydrated cake and the treated pigment may be easily dispersed in other water-base or emulsion-type cosmetic bases (and will not easily precipitate) without the use of a large volume of surface active agents which could cause irritation of the skin.

In case that the skin is coated with the water dispersion type make-up cosmetic, or emulsion type make-up cosmetic thus obtained, the make-up cosmetic strongly adheres to the skin uniformly. The treated pigment on the skin loses spontaneously the water on the boundaries of the pigment, so that it remains adhered strongly on the skin as hydrophobic particles which are hardly wet with water. Consequently, it becomes an excellent cosmetic in that it maintains its cosmetic effects for a long time without being degraded.

The present invention is further described based upon specific Examples which are not intended to limit the scope of the present invention.

EXAMPLE 1

(1) Extender pigment and pearl pigment treated with aluminum N-myristoyl-L-glutamate Sodium N-myristoyl-L-glutamate was added to a suspension in which 30 g of sericite had been suspended in 4 liters of water. Then, stirring was fully carried out. Into this suspension was added 60 ml of a 20% aqueous solution of aluminum sulfate in 10 minutes. Then, further stirring was carried out for 10 minutes. Thereafter, the suspension was dehydrated by means of a basket type centrifuge. Then, drying was carried out at 110° C. in a hot-air drying apparatus to produce about 1 kg of a dried product. The dried product thus obtained was crushed by means of a high-speed mixer (hexyl mixer) to a light degree.

The same procedures as just mentioned above were repeated with respect to mica powder, talc, and mica titan.

(2) Pigment treated with aluminum N-myristoyl-L-glutamate or squalene 40 g of sodium N-myristoyl-L-glutamate was added to a suspension in which 0.5 kg of titanium oxide and 0.5 kg of talc had been suspended in 4 liters of water. Then, stirring was fully carried out. Into this suspension was added dropwise 80 ml of a 20% aqueous solution of aluminum sulfate over 10 minutes. After stirring and mixing for an additional 10 minutes, a mixture of 30 g of squalene and 30 g of toluol was added and stirred for 10 min. The succeeding procedures were carried out following those in (1) above. Thus, about 1 kg of white dried product was obtained.

The same procedures were repeated with respect to yellow iron oxide, red iron oxide, black iron oxide.

| Powder foundation | | |
| --- | --- | --- |
| Composition 1: | treated sericite | 50 wt. parts |
| | treated talc | 8.1 wt. parts |
| | treated mica powder | 3.0 wt. parts |
| | treated mica titan | 3.0 wt. parts |
| | treated titanium oxide | 19.0 wt. parts |
| | treated yellow iron oxide | 3.0 wt. parts |
| | treated red iron oxide | 1.0 wt. parts |
| | treated black iron oxide | 0.2 wt. parts |
| Composition 2: | Squalene | 5.0 wt. parts |
| | methylpolysiloxane | 3.0 wt. parts |

| -continued | | |
| --- | --- | --- |
| Powder foundation | | |
| | isopropyl myristinate | 2.0 wt. parts |
| | paraffin | 1.0 wt. parts |
| | surface active agent | 1.0 wt. parts |
| | antiseptic | 0.2 wt. parts |
| | perfume | 0.5 wt. parts |

Composition 1 was mixed by means of a hexyl mixer and crushed by atomizer. Into the crushed mixture was added Composition 2 as heated, and then mixed by means of the hexyl mixer. Then, the mixture was crushed again by the atomizer. The mixture thus crushed was charged and molded in a dish, thereby producing a finished product.

The powder foundation thus obtained is a two-way type powder foundation with excellent water-repellent property which can be applied by means of a water-free sponge or by means of a sponge containing water.

By comparing the powder foundation as obtained above and a powder foundation obtained by adding the above Composition 2 to the same pigments and body extenders as employed in Composition 1 but which are treated with methylhydrodienepolysiloxane following the same procedures as above, it is revealed that the powder foundation utilizing the pigment treated according to the present invention is superior to the control powder foundation from the standpoint of extendability onto a sponge, adherability onto the skin, smoothness after being applied as make-up, and maintenance of the cosmetic on the skin.

EXAMPLE 2

(1) Mixed pigments treated with calcium N-stearoyl-N-methyl-$\beta$-alanine 40 g of sodium N-stearoyl-N-methyl-$\beta$-alanine was added to a suspension in which a total weight of 1 kg of a mixture of 45 parts sericite, 200 parts mica powder, 120 parts talc, 100 parts kaoline, 90 parts titanium oxide, 20 parts yellow iron oxide, and 20 parts red iron oxide had been suspended into 4 liters of water. Then, the suspension was well stirred.

Next, 80 ml of a 15% aqueous solution of zinc sulfate was mixed dropwise into this suspension over 10 minutes under stirring. After stirring another 10 minutes, 50 g of liquid paraffin was gradually added to the suspension and then stirring was carried out for 10 minutes. The suspension thus obtained was concentrated through dehydration by means of a basket type centrifuge to produce 2.2 kg of paste-like cake containing about 50% moisture.

| Foundation | | |
| --- | --- | --- |
| Composition 1: | treated mixed pigment (hydrated) | 40 wt. parts |
| | liquid paraffin | 3.5 wt. parts |
| | squalene | 5.0 wt. parts |
| | stearyl alcohol | 3.0 wt. parts |
| | lanolin | 1.0 wt. parts |
| | surface active agent | 1.5 wt. parts |
| | antiseptic | 2.0 wt. parts |
| Composition 2: | propylene glycol | 5.0 wt. parts |
| | ion-exchanged water | 40.0 wt. parts |
| | perfume | 0.8 wt. parts |

Compositions 1 and 2 were heated up to 70° C. independently. Then, Composition 2 was added over 5 minutes to Composition 1 which was being stirred by means of a homogenizer. Thereafter, stirring was carried out for another 10 minutes for emulsification. Then, it was cooled and charged into a vessel to produce a product.

The foundation thus obtained was an excellent cosmetic with uniform make-up finish, strong adherability to the skin, and make-up degradation resistance.

EXAMPLE 3

(1) Magnesium N-lauroyl-L-methylglycine powder

Into 1 liter of 8% of sodium N-lauroyl-L-methylglycine which had been heated up to 60° C. was dropped 10% of an aqueous solution of magnesium sulfate in an amount of 1.2 molar equivalents with respect to the former. Then, stirring was continued for 10 minutes. The reaction mixture was concentrated through precipitation, and then the concentrated reaction mixture was dried through spraying and then atomizer-crushed to obtain about 85% of white powder.

| Rouge for cheek | | |
|---|---|---|
| Composition 1: | sericite | 30 wt. parts |
| | nylon powder | 10.0 wt. parts |
| | talc | 30.0 wt. parts |
| | titanium oxide | 3.0 wt. parts |
| | red iron oxide | 2.0 wt. parts |
| | magnesium N—lauroyl-L-glycine | 7.2 wt. parts |
| Composition 2: | methylpolysiloxane | 12.0 wt. parts |
| | myristic acid | 3.0 wt. parts |
| | lanolin | 2.0 wt. parts |
| | squalene | 2.0 wt. parts |
| | perfume | 0.8 wt. parts |

After Composition 1 was mixed by means of a hexyl mixer, it was crushed by means of an atomizer. Composition 2 as dissolved through heating was added and mixed with Composition 1 thus crushed, and the atomizer-crushing was carried out. The atomized mixture was press-molded into a vessel to produce a product.

EXAMPLE 4

(1) Mixed powder of aluminum N-stearoyl-L-glutamate and zinc N-oleyl-L-glutamate 1 liter of 15% aqueous solution of a mixture of sodium N-stearoyl-L-glutamate and sodium N-oleyl-L-glutamate (the ratio being 6:4) was heated up to 50° C. Into this solution was added 10% aqueous solution of zinc acetate in an amount of 1.0 equivalent with respect to the former mixture. Then, stirring was continued for 10 minutes. The procedure of Example 3 was then followed to obtain about 155 g of white powder.

| Eye-shadow | | |
|---|---|---|
| Composition 1: | mica titan | 30 wt. parts |
| | talc | 22.0 wt. parts |
| | sericite | 20.0 wt. parts |
| | red iron oxide | 2.0 wt. parts |
| | ultramarine blue | 2.0 wt. parts |
| | white powder as obtained above [Example 4 (1)] | |
| Composition 2: | methylpolysiloxane | 5.0 wt. parts |
| | isopropyl myristate | 5.0 wt. parts |
| | liquid paraffin | 5.0 wt. parts |
| | lanolin | 1.0 wt. parts |

Compositions 1 and 2 were mixed into a product in a manner similar to that of Example 3.

The rouge for cheek of Example 3 and eye-shadow of Example 4 are more strongly and uniformly adhesive and low in make-up degradation due to the addition of the treated pigment according to the present invention.

As mentioned above, the cosmetic composition for make-up according to the present invention has an excellent protective property to the skin, has good affirmity to the skin, nice touch to the skin, excellent extendability to the skin and stability due to the addition of the N-acylamino acid metal salt and/or pigment or extender pigment treated with the N-acylamino acid metal salt.

The cosmetic composition according to the present invention may include two or more of the N-acylamino acid metal salts.

Moreover, the discussion as stated above is directed to the cosmetic composition for make-up, but the present invention is applicable as a cosmetic for foundation.

What is claimed is:

1. A cosmetic composition containing a pigment or an extender pigment the surfaces of which are coated with 0.5–10 weight %, based on the weight of said pigment or extender pigment, of metal salt of N-acylamino acid selected from the group consisting of (I), (II) and (III):

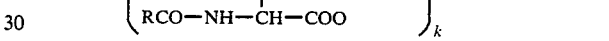

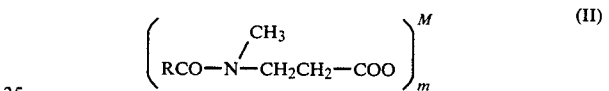

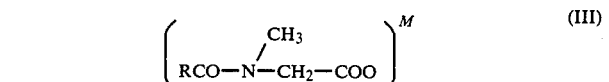

wherein RCO denotes a residue of capric acid, lauric acid, myristic acid, palmitic acid, stearic acid, or oleic acid; M denotes aluminum atom, magnesium atom, calcium atom, zinc atom, zirconium atom, or titanium atom; k is an integer of 1 to 3; l is an integer of 1 to 2; and m is an integer of 1 to 4; in combination with cosmetically acceptable ingredients.

2. The cosmetic composition of claim 1, wherein the pigment or extender pigment having surfaces coated with the N-acylamino acid metal salt is further coated with a member selected from the group consisting of liquid paraffin, squalene, petrolatum, microwax, polyisobutylene, myristic acid, stearic acid, lauric acid, selemine, isopropylmyristate, myristyldodecanol, coconut oil, castor oil, lanoline, beeswax, olive oil, stearyl alcohol, milk oil, oleyl alcohol, and monostearic gylceride.

3. The cosmetic composition of any one of claims 1 or 2 wherein the N-acylamino acid is one selected from the group consisting of N-acyl-N-methyl-glycine, N-acyl-N-methyl-β-alanine, and N-acyl-L-glutamic acid.

4. The cosmetic composition of claim 3, wherein the N-acylamino acid is N-acyl-L-glutamic acid.

5. The cosmetic composition of any one of claims 1 or 2, wherein the pigment or extender pigment is at least one member selected from the group consisting of titanium oxide, zinc oxide, zirconium oxide, red iron oxide, yellow iron oxide, black iron oxide, ultramarine blue, Berlin blue, chromium oxide, chromium hydroxide, talc, kaoline, white mica powder, sericite, magnesium carbonate, calcium carbonate, aluminum silicate, magnesium silicate, calcium silicate, clay, mica titan, bismuth oxychloride, nylon powder, polyethylene powder, coal tar coloring material, and natural coloring matter.

6. In a cosmetic composition wherein an amino acid is employed as an emulsifier or dispersing agent, the improvement comprising employing as the amino acid a water-insoluble metal salt of N-acylamino acid selected from the group consisting of (I), (II) and (III):

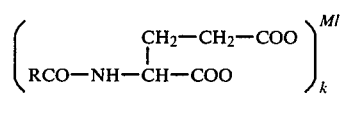
(I)

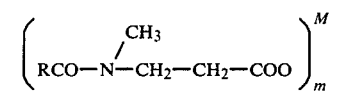
(II)

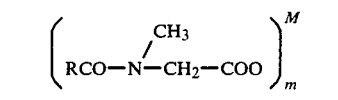
(III)

wherein RCO denotes a residue of capric acid, lauric acid, myristic acid, palmitic acid, stearic acid, or oleic acid; M denotes aluminum atom, magnesium atom, calcium atom, zinc atom, zirconium atom, or titanium atom; k is an integer of 1 to 3; l is an integer of 1 to 2; and m is an integer of 1 to 4.

7. A cosmetic composition comprising a pigment and an extender pigment the surfaces of which are coated with 0.5–10 weight %, based on the weight of said pigment and extender pigment, of a metal salt of N-acylamino acid selected from the group consisting of (I), (II) and (III):

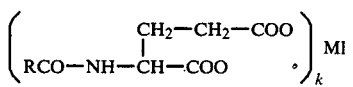
(I)

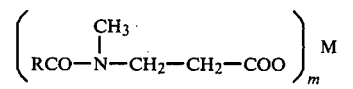
(II)

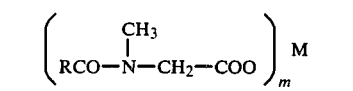
(III)

wherein RCO denotes a residue of capric acid, lauric acid, myristic acid, palmitic acid, stearic acid, or oleic acid; M denotes aluminum atom, magnesium atom, calcium atom, zinc atom, zirconium atom, or titanium atom; k is an integer of 1 to 3; l is an integer of 1 to 2; and m is an integer of 1 to 4; in combination with cosmetically acceptable ingredients.

* * * * *